United States Patent [19]

Swanson et al.

[11] Patent Number: 5,239,988
[45] Date of Patent: Aug. 31, 1993

[54] CARDIO-PULMONARY RESUSCITATION AID

[75] Inventors: John L. Swanson; Caterina V. Hardy, both of P.O. Box 1315, MacKay QLD 4740; Alan J. Blair; Edith R. Blair, both of Mt. Pleasant, all of Australia

[73] Assignees: John L. Swanson; Caterina A. Hardy, MacKay, Australia

[21] Appl. No.: 799,972

[22] Filed: Nov. 29, 1991

Related U.S. Application Data

[63] Continuation-in-part of Ser. No. 459,771, Jan. 12, 1990, abandoned.

[51] Int. Cl.$^5$ ............................................. A61H 31/00
[52] U.S. Cl. ....................................... 128/28; 434/265
[58] Field of Search .................. 368/107, 108; 128/28; 434/265, 262

[56] References Cited

U.S. PATENT DOCUMENTS

| | | | |
|---|---|---|---|
| 3,802,417 | 4/1974 | Lang | 128/30.2 X |
| 4,193,064 | 3/1980 | Snyder | 340/309.15 X |
| 4,236,240 | 11/1980 | Yoshida | 368/107 |
| 4,360,345 | 11/1982 | Hon | 434/262 |
| 4,491,424 | 1/1985 | Cohens | 368/89 |
| 4,583,524 | 4/1986 | Hutchins | 434/262 X |
| 4,588,383 | 5/1986 | Parker et al. | 434/265 |
| 4,797,104 | 1/1989 | Laerdal et al. | 434/265 |
| 4,828,501 | 5/1989 | Igenito et al. | 434/262 X |
| 4,863,385 | 9/1989 | Pierce | 434/265 |

OTHER PUBLICATIONS

Jogger's Pacesetter, Butler Associated Goals; May 5, 1980.

Primary Examiner—Gene Mancene
Assistant Examiner—L. Thomas
Attorney, Agent, or Firm—Edwin D. Schindler

[57] ABSTRACT

A cardio-pulmonary resuscitation (CPR) aid is disclosed. It is in the form of a wrist watch (10) having a set of auxiliary push buttons (13, 14 and 15). When a push button (13, 14 or 15) is pressed, audible signals are emitted from a beeper (16) at a rate dependent on which of the push buttons (13, 14 or 15) is pressed for use in timing external heart massage. The appropriate one of a set of push button lights (23, 24 or 25) associated with respective ones of the push buttons (13, 14 or 15) flashes in synchronism with the audible signals for timing CPR in noisy areas. The watch also records the elapsed time since the initiation of the CPR signals and the number of timing signals produced.

17 Claims, 5 Drawing Sheets

CARDIO-PULMONARY RESUSCITATION AID

This application is a continuation-in-part of application Ser. No. 07/459,771, filed Jan. 12, 1990, now abandoned.

BACKGROUND OF THE INVENTION

This invention relates to an improved cardio-pulmonary resuscitation aid and in particular it relates to a watch assembly operable to provide aid for cardio-pulmonary resuscitation.

Cardio-pulmonary resuscitation techniques for reviving patients are well known and their use is widespread. Such techniques are extremely effective when correctly carried out and have resulted in the saving of many lives. While many people have a basic understanding of the technique, most people are untrained and are incapable of effectively administering cardio-pulmonary resuscitation techniques in an emergency. One of the critical factors in the technique is the timing of the chest compressions. This varies with the age of the patient. Skilled resuscitators are practiced in performing the chest compression function at a relatively constant predetermined rate. Various techniques have evolved to enable the correct rate to be achieved, but practice is still needed to maintain reliable performance of the resuscitation technique.

In an emergency, the time taken to commence resuscitation is critical to the survival chances of the patient and it is desirable that there be no delay in commencing the technique. Thus a person skilled in the art of cardio-pulmonary resuscitation has a far greater chance of reviving a patient than does a person who is aware of the technique and its application, but who may have lost the necessary skill to accurately perform the required chest compressions.

Unfortunately, while the basic technique is relatively easy to remember, it is difficult for most people to remember the actual rate required for different age groups and the techniques to perform the compressions at the required rate. Furthermore, the duration of cardio-pulmonary resuscitation prior to clinical care may influence doctors' decisions as to the further treatment required for a patient, and this information is rarely recorded in any way during emergency treatment by other than highly experienced personnel.

Known CPR devices permit the selection of a discrete range of compression rates corresponding to the compression rates appropriate for patients within various age groups.

It is also desirable that on occasions CPR be performed at other rates more appropriate to individual circumstances. There is thus a need for a device which will permit an individual compression rate to be selected whilst maintaining the basic requirement for easy access to the three basic rates.

It is also known that when monitoring a pulse rate it is difficult to maintain observation of a patient because of the need to visually monitor a watch at the same time. It is thus desirable that a pulse may be measured or monitored without the necessity to cease visual observation of a patient.

There are also occasions when either or both audible and visual indication for either compression or inflation may be required or preferred to be suppressed or muted. Accordingly it is desirable that CPR aids facilitate the optional selection by the user of either form of indicator for either purpose.

It is also desirable that the operator periodically check the carotid artery for signs of a pulse. Typically this occurs at the end of the first minute of CPR. If no pulse is detected resuscitation is recommended and the pulse checked again every two minutes thereafter. During training many students experience difficulty in memorising pulse check sequences and some students count with fingers as an aide memoire. Accordingly it is desirable the CPR prompts and training aids preferably include means for providing prompting to assist the accurate checking of the carotid artery.

This invention aims to alleviate the abovementioned problems and to provide a cardio-pulmonary resuscitation aid which will be reliable and efficient in use. Other objects and advantages of this invention will hereinafter become apparent.

SUMMARY OF THE PRESENT INVENTION

With the foregoing and other objects in view, this invention in one aspect resides broadly in a watch assembly operable to provide aid for cardio-pulmonary resuscitation, said watch assembly having time keeping and time display means whereby said watch is operable in a time keeping mode, cardio-pulmonary resuscitation aid means whereby said watch is operable in a cardio-pulmonary resuscitation mode, and mode selection means operable to select said time keeping mode or said cardio-pulmonary resuscitation mode, wherein said cardio-pulmonary resuscitation aid means includes:

chest compression indication means which provides recurring chest compression signals;

switching means for selecting a desired one of a plurality of chest compression signal rates indicated by identification means associated with said switching means;

pulmonary inflation indication means which provides regular pulmonary inflation signals in accordance with the selected chest compression signal rate;

counting means for counting the total number of chest compression signals;

timing means which records the elapsed time corresponding to the total chest compression signals counted, and counting and timing display means which provides a visual display of the output of said counting means and said timing means.

Preferably, the chest compression indication means includes an audible alarm which will repeatedly sound at the desired chest compression rate and/or visual indication means which will provide a corresponding display of the selected compression rate. Alternatively, or in addition, visual indication means may be provided, and may take the form of a visual display corresponding to the desired compression rate.

The audible alarm may also be adapted to produce lung inflation synchronization signals at a selected lung inflation rate. The lung inflation rate may be any desired rate, but it is preferred that it be programmed to a selected fraction of the chest compression rate whereby the lung inflation rate may be varied proportionally to the chest compression rate by operation of the switching means.

The switching means may include a plurality of switch assemblies, for instance three switch assemblies, and each of the switch assemblies may be provided with a respective identification means appropriate to a selected compression rate. The identification means may be the numerals 60, 80 and 100 applied to respective ones of the switching means corresponding to the compression rates appropriate for patients within various age groups and for the number of operators performing cardio-pulmonary resuscitation.

Alternatively, the identification means may include symbols relating to the physical condition of patients and/or the number of available operators, the symbols being applied to respective ones of the switch assemblies. If desired, the identification means may include colours, such as yellow, blue and red applied to respective switch assemblies.

In a preferred form, each said switch assembly includes visual indicator means which when activated indicate an actuated switch assembly. Preferably the visual indicator means and said audible alarm are simultaneously actuated. Suitably the visual indicator means is a light which flashes at the selected time interval in synchronism with the audible signal.

The timing means may be arranged to commence timing upon activation of the chest compression indication means. Preferably the arrangement is such that the counting and timing display means is numerical and indicates the duration of the cardio-pulmonary resuscitation as well as the rate and/or number of chest compressions used during that period.

If necessary, a plurality of displays may be provided to display the duration of periods at varying rates of compression such as, for example, at start up and during subsequent treatment. This arrangement has the advantage that, when clinical care becomes available, the clinicians may review the time history of the cardio-pulmonary resuscitation to determine the duration and timing of the CPR operations carried out to that point in time. Alternatively, a single numerical display may be provided, and may be utilised for the successive display of a plurality of rates.

Preferably the watch has an analogue/digital display having a second hand which sweeps a watch face divided into quarters whereby the watch may be conveniently usable for checking pulse rates. Of course the timing device can be in the form of a clock or the like which may be advantageously used as a fixed installation in hospital wards, ambulances and the like. In such installations, the digital display may be an L.C.D. type display so as to provide easy recognition in fully lit areas.

Preferably the watch includes a plurality of function buttons and said switching means includes actuating means responsive to one of a number of coded options selectable upon operation of appropriate ones of said plurality of function buttons, and may include as one option thereof the facility to vary the chosen compression rate from one of the three standard rates coded as fixed switching options.

In a preferred embodiment the invention includes a countback assembly which provides a visual and/or audile indication upon the elapsing of a predetermined or preselected time period. Preferably the predetermined time period is 15, 30 and 60 seconds thereby facilitating the measurement or monitoring of a patients pulse without having to cease visual observation.

Suitably the timing device includes muting means adapted to vary the production of visual and audile indications in respect of both compression and inflation rates. The muting means may for example be an array of switching devices each selectively programmed to produce a predetermined result, or the muting means may be simple on-off switches. Attenuating means may also be provided to vary the amplitude of the indications. However preferably the muting means includes selection switching means operable to select one of a number of coded options generated upon operation of appropriate ones of said plurality of function buttons. Suitably one of the coded options includes the option of generating indications of the need to check the pulse of a patient.

In a further embodiment a mode button is provided which actuates a cyclic display of functions which may be selected by stopping the display at the appropriate function. This may include functions for adult, child or infant as well as a function for changing the inflation timing and or compression rate for operations by a single operator (two inflations every fifteen compressions), or for operation by two operators (one inflation every five compressions), and a function for inflation cycle only for use on patients with a pulse or for practicing cardio-pulmonary resuscitation.

In a further aspect, this invention resides in a watch assembly operable to provide aid for cardio-pulmonary resuscitation, said watch assembly having time keeping and time display means whereby said watch is operable in a time keeping mode, cardio-pulmonary resuscitation aid means whereby said watch is operable in a cardio-pulmonary resuscitation mode, and mode selection means operable to select said time keeping mode or said cardio-pulmonary resuscitation mode, wherein said cardio-pulmonary resuscitation aid means includes:

chest compression indication means which provides recurring chest compression signals;

switching means for selecting a desired one of a plurality of chest compression signal rates indicated by identification means associated with said switching means;

visual indicator means operatively associated with said switching means whereby a respective one of said visual indicator means is activated when a chest compression rate is selected, said chest compression indication means and a respective one of said visual indicator means being simultaneously and repetitively activated at the selected desired chest compression rate, and pulmonary inflation indication means which provides regular pulmonary inflation signals in accordance with the selected chest compression signal rate.

In another aspect this invention resides broadly in a cardio-pulmonary resuscitation aid including:

chest compression indication means which provides recurring chest compression signals, said indication means having an audible alarm for producing chest compression signals at a selected desired chest compression rate and chest compression display means which provides a visual display corresponding to the selected desired chest compression signal rate;

switching means for selecting a desired one of a plurality of chest compression signal rates indicated by identification means, said switching means having three switch assemblies each provided with identification means in the form of the numerals 60, 80 and 100 applied to respective ones of said switch assemblies and including visual indicator means simultaneously actuated with said audible alarm and which when activated indicate an actuated switch assembly;

pulmonary inflation indication means which provides regular pulmonary inflation signals in accordance with the selected chest compression signal rate;

counting means for counting the total number of chest compression signals;

timing means which records the elapsed time corresponding to the total chest compression signals counted, and counting and timing display means which provides a plurality of numerical displays indicating the output of said counting means for each selected desired chest compression rate and the output of the timing means indicating the elapsed time corresponding to the total chest compression signals counted.

BRIEF DESCRIPTION OF THE DRAWINGS

In order that this invention may be more readily understood and put into practical affect, reference will now be made to the accompanying drawings which illustrate a preferred embodiment of a wrist watch made according to the present invention, wherein.

DESCRIPTION OF THE PREFERRED EMBODIMENT

Figure 1:
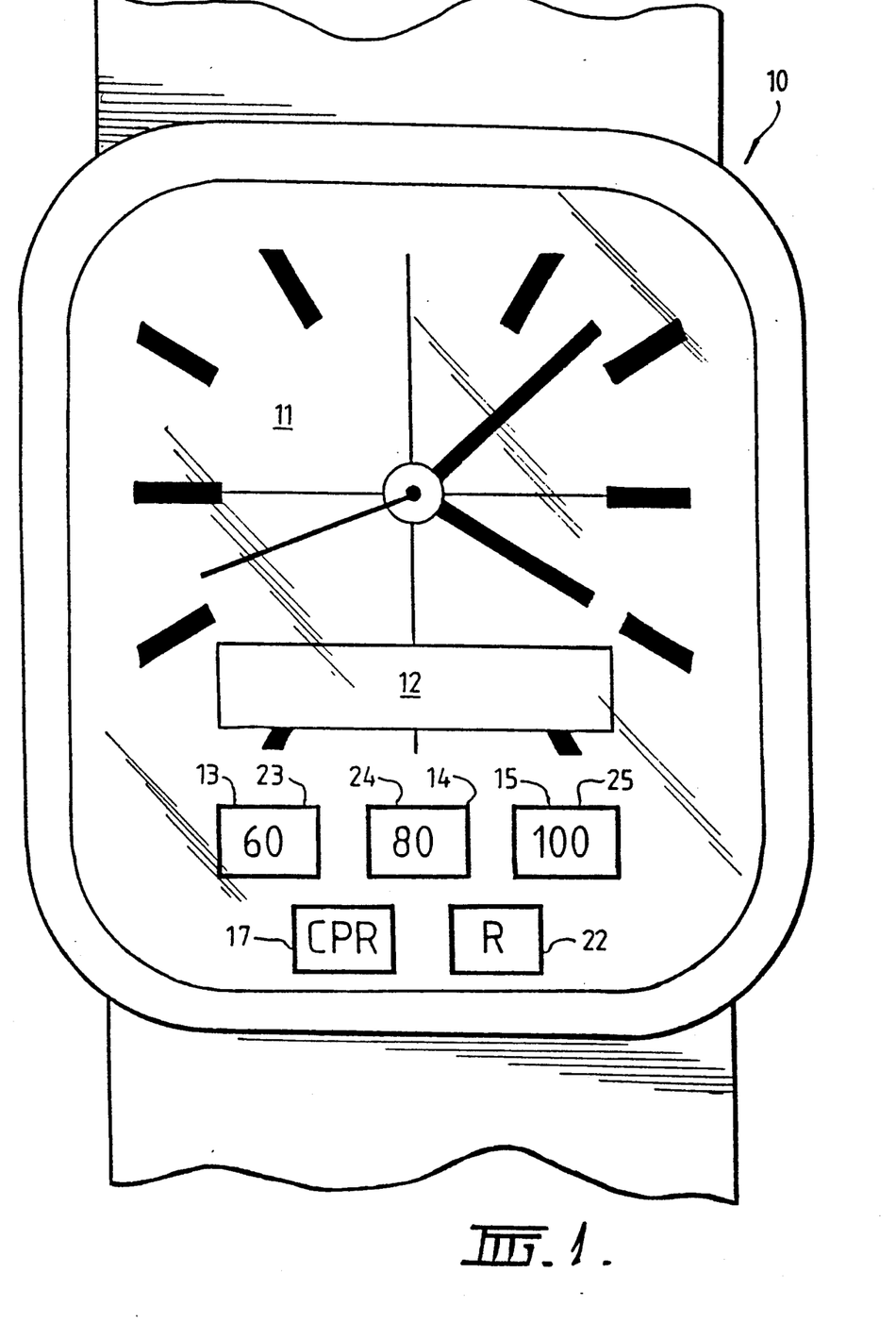
FIG. 1 illustrates an analog-display wrist watch according to the invention.

As shown in FIG. 1, the analog-display wrist watch 10 is a modified watch having a conventional watch face 11 provided with second, minute and hour hands and a digital time display 12. In addition, the watch face 11 supports three colour-coded buttons 13, 14 and 15 which in this instance are marked with the numerals 60, 80 and 100. These numbers represent the three rates of chest compression commonly required for performing cardio-pulmonary resuscitation.

The buttons 13, 14 and 15 incorporate liquid crystal button displays 23, 24 and 25 respectively, and are colour coded. The button 13 is yellow, the button 14 is blue and the button 15 is red. An audible alarm or beeper 16 is built into the watch 10 and this is adapted to provide a repeating audible signal at the frequency indicated on the control buttons, namely 60 signals per minute, 80 signals per minute and 100 signals per minute respectively. It will also be seen that the watch face 11 includes quarter-minute segments to facilitate measuring of fifteen-second pulse rates.

In an emergency, a person wearing the watch 10 can apply cardio-pulmonary resuscitation techniques in an accurate manner by firstly pressing the appropriate button 13, 14 or 15 in accordance with the age group of the patient, or the number of operators performing CPR, and then regulating their rate of manual chest compressions to correspond to that indicated by the audible signal provided by the watch 10 or by the flashing of the selected button display 23, 24 or 25 which flashes in synchronism with the audible signal whereby the operator or operators may readily check that the appropriate rate is being used.

Thus in circumstances where external noise may drown out the noise from the beeper 16, the operator can maintain the selected rate by observing the watch face 11. In other circumstances in which the beeper 16 can be clearly heard, the person may direct their attention elsewhere while at the same time maintaining an accurate rate of chest depression in time with the audible signal.

Figure 2:
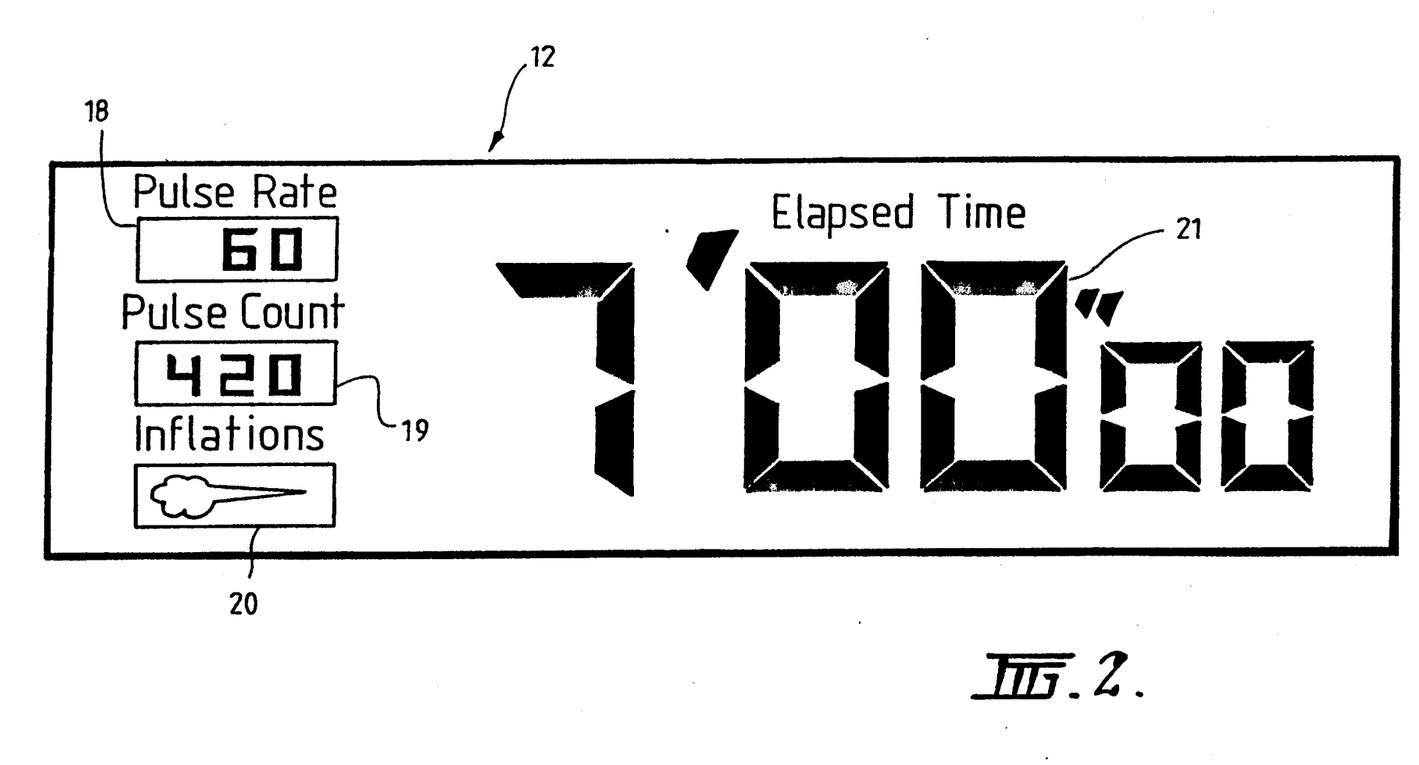
FIG. 2 illustrates the digital display of the wrist watch illustrated in FIG. 1.

In use, the mode button 17 is pressed to activate the CPR functions and the appropriate button 13, 14 or 15 is pressed. The digital time display 12 is automatically replaced by the display shown in FIG. 2. This includes a pulse rate display 18, a pulse counter 19 and an inflation indicator 20. The latter is displayed at the appropriate pulse count sequence, depending upon the button 13, 14 or 15 pressed, to indicate the appropriate timing for lung inflations such as by mouth-to-mouth resuscitation. At the same time, the stop watch display 21 provides the duration of resuscitation. This display remains as a reference until the reset button 22 is pressed. A further alarm or pause in the sequence may be provided to indicate to the operator to stop compressions and check for a patient's pulse.

Figure 4:
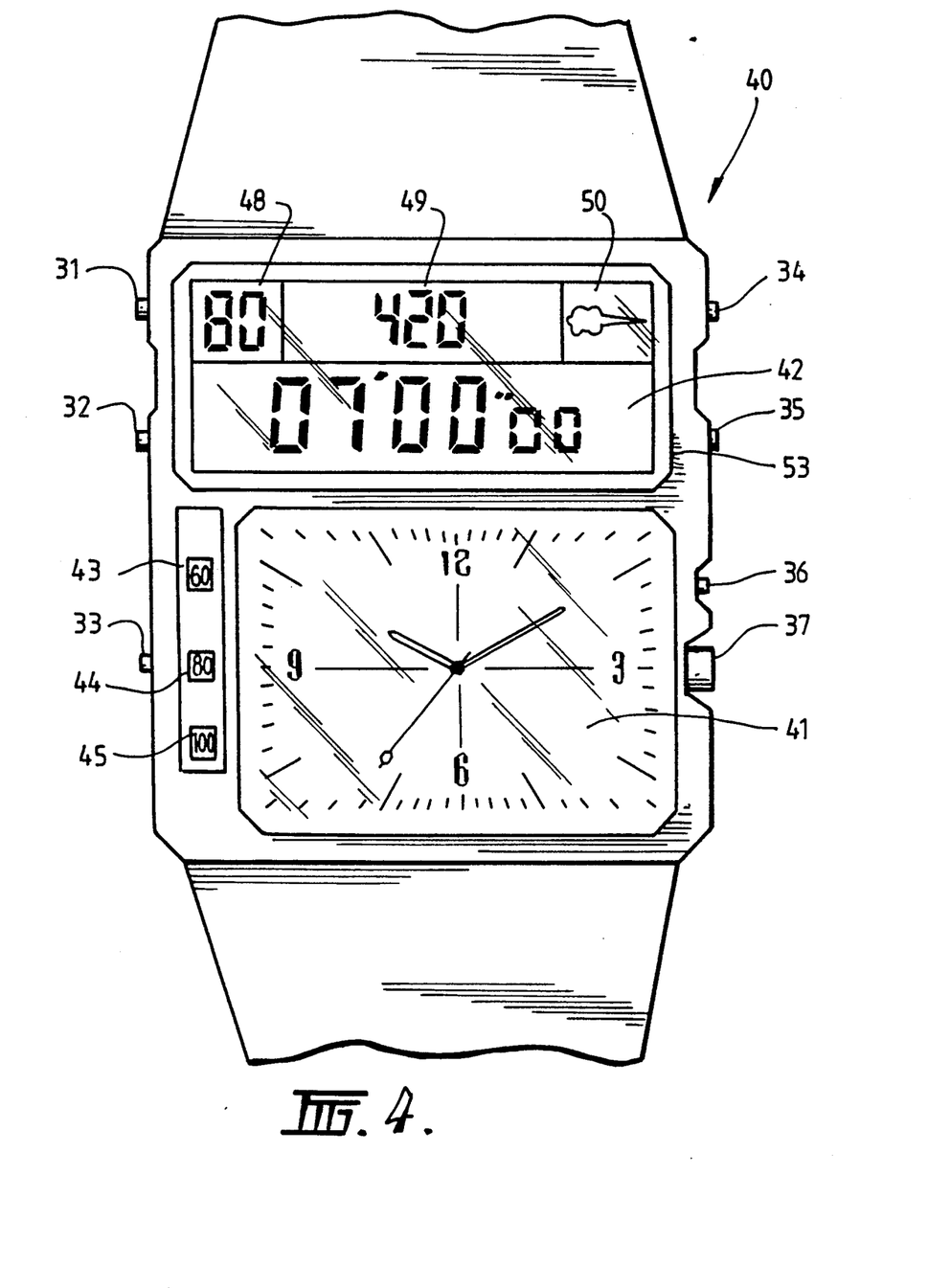
FIG. 4 illustrates another analog-display wrist watch according to the invention.
Figure 5:
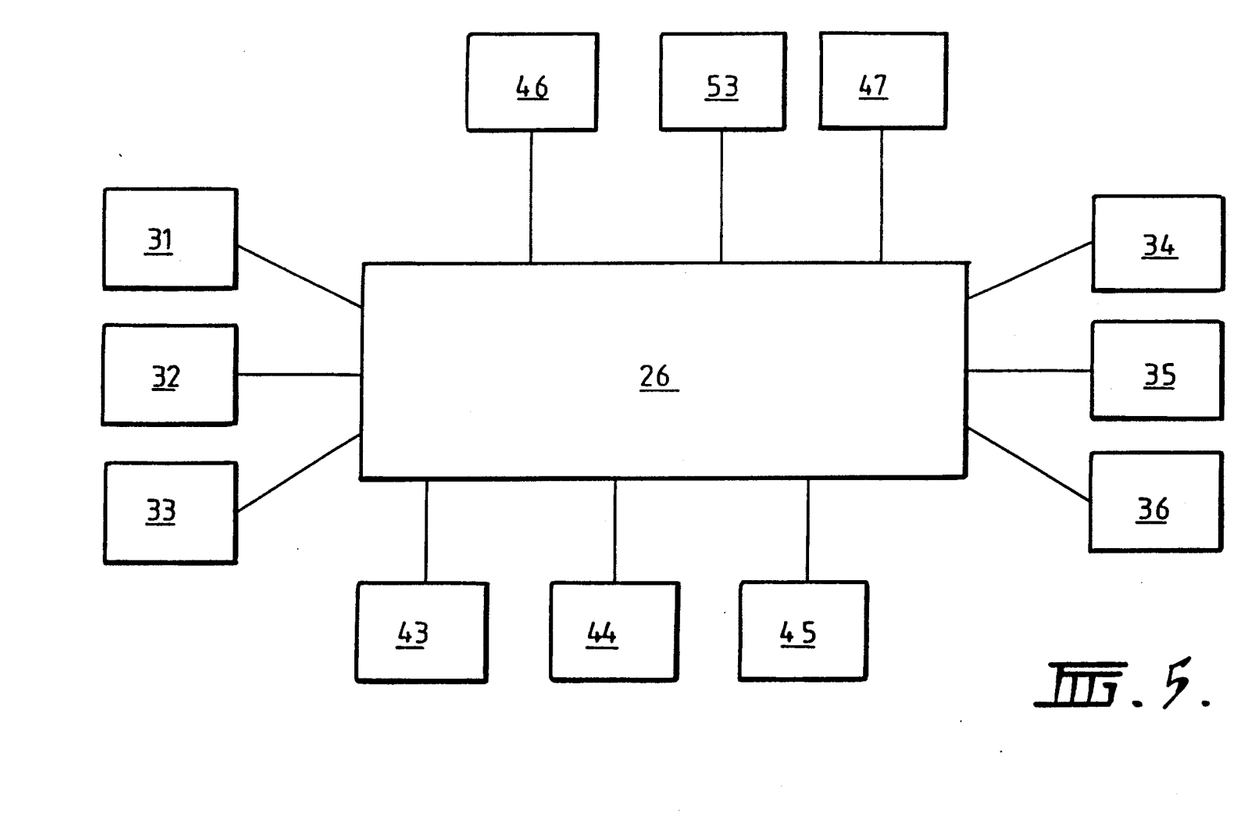
FIG. 5 is a block diagram of the wrist watch shown in FIG. 4.

As can be seen in FIGS. 4 and 5, the analog-display wrist watch 40 is a modified watch having a conventional watch face 41 provided with second, minute and hour hands and a digital time display 42. In addition, the watch face 41 supports three colour-coded buttons 43, 44 and 45 which in this instance are marked with the numerals 60, 80 and 100. These numbers represent the three rates of chest compression commonly required for performing cardio-pulmonary resuscitation.

The buttons 43, 44 and 45 incorporate liquid crystal button displays (not shown) and are colour coded. The button 43 is yellow, the button 44 is blue and the button 45 is red. It will also be seen that the watch face 41 includes quarter-minute segments to facilitate measuring of fifteen-second pulse rates.

An LCD display panel 53 which in normal time-keeping mode displays the time as at 42, but in CPR mode the digital time display 42 becomes an information panel. The LCD display in CPR mode includes a pulse rate display 48, a pulse counter 49 and an inflation indicator 50.

The watch includes function buttons 31 to 36 which are operable in conventional manner by depression to enable the multi-functional capabilities of the device to be utilised. The watch also includes a standard winding crown 37.

An audible alarm or beeper 46 is built into the watch 40 and this is adapted to provide a repeating audible signal at the frequency selected, namely 60 signals per minute, 80 signals per minute, 100 signals per minute or at another selected frequency of up to 140 signals per minute.

The selected rate is displayed at 48 and the stop watch display indicates the duration of resuscitation. This display remains as a reference until reset. A further alarm or pause in the sequence may be provided to indicate to the operator to stop compressions and check for a patient's pulse.

A three stage count down timer 47 is incorporated into the time mode of the watch and provides a digital (L.C.D.) Liquid Crystal Quartz Display and alarm signal. This will enable a patient's pulse to be taken without reference to a seconds hand. A time interval of 15, 30 or 60 seconds is selected and a count back timer counts the seconds to zero when an alarm sounds.

The invention can be called upon to provide precise time pulsed indication means in both audio and visual references. The three base rates for chest compressions of 60, 80 and 100 PPM have been provided. Operator programmable means can also be provided to indicate rates up to 140 PPM if desired.

In use, the appropriate ones of function buttons 31 to 36 are operated to select the desired operating mode. Thus for instance various combinations of the function keys may be used to set the time, set the date, set the alarm or set a 24 hour day display. These function buttons are also operated to enter the special CPR modes of the invention. Thus to utilise the count-down facility to facilitate the taking of a patient's pulse, function button 34 is depressed three times, button 35 is depressed to select the correct count-back i.e. 15, 30 or 60 seconds for pulse checking, button 31 is depressed to start the count-down, and the alarm 46 will sound when the chosen period has elapsed.

To operate in CPR mode, button 31 is depressed to shift out of timekeeping mode, and upon depression of button 32 one of the standard three compression rates with either one- or two-person operation may be selected and commenced by depression of button 33. A compression beeping sound at the selected rate will be heard and the appropriate LED will flash in synchronization.

To optionally select the compression rate, the button 35 is depressed twice and button 34 depressed to select the desired rate which will be indicated in display 48 and will advance numerically as button 34 remains depressed. The rate is set by depressing button 35. Upon commencement by depression of button 33, the compression beeping sound at the selected rate will be heard and all three LEDs will flash in synchronization.

Both audio and video signals can be muted leaving the digital display to count the compression pulses and elapsed time through the stop watch display. This will permit classroom training practice to check proficiency standards of the student. Inflation sequences can be provided in the audio by incorporating a dual tone signal for recognition. This dual effect can be selectively muted if desired to provide a continuous and constant pulse at the selected rate per minute, i.e. mono tone only.

To optionally select a particular mute combination or other function modes, button 35 is depressed when operating in the CPR mode and the range of available combinations is displayed in the LCD display 53. Before operation in the CPR mode the mute combination currently selected may be determined by depressing button 36.

Indicative of the range of mute combinations and function modes possible are the following:
automatic pulse check.
compression sound, LED flashing and inflation sound.
no compression sound, there is LED flashing and inflation sound.
compression and inflation sound, no LED flashing.
no compression sound or LED flashing, there is inflation sound.
compression sound and LED flashing, no inflation sound.
no compression or inflation sound, there is LED flashing.
no LED flashing or inflation sound, there is compression sound.
no compression sound, no inflation and no LED flashing.

The automatic pulse check (APC) function system may be conveniently incorporated as one of the function modes in the system for accessing combinations within the "mute" operating system. This check operates as an automatic switching arrangement and provides regular distinctive audible and/or visual prompts commencing at the end of the first minute of CPR so that the operator will be reminded to check the pulse at the carotid artery. The APC operates as an automatic switching arrangement which when selected freezes the LCD for five seconds and audio/visual signals for 4.5 seconds. Preferably the APC function is only operable with a NO MUTE function mode.

Figure 3:
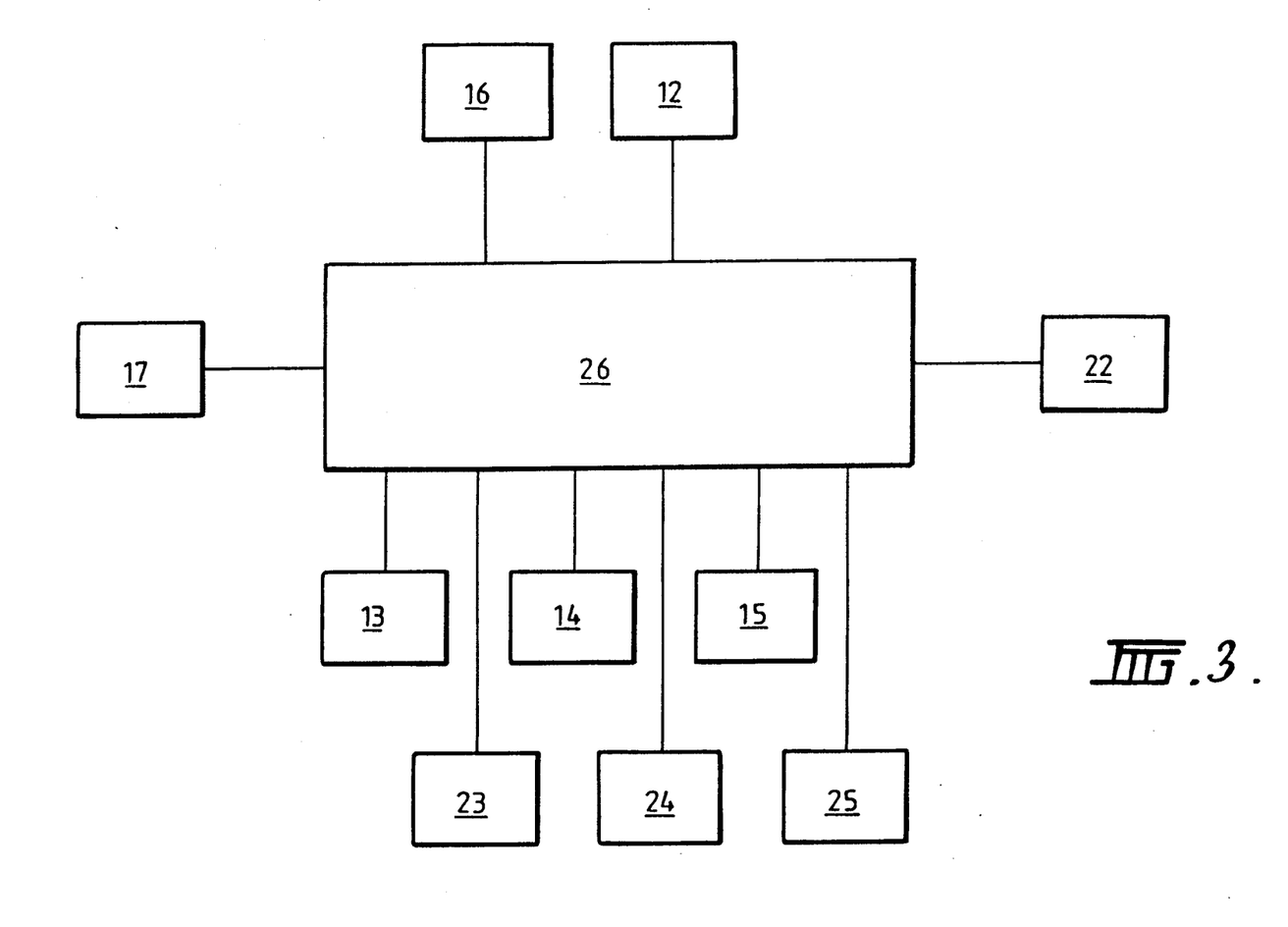
FIG. 3 is a block diagram of the wrist watch shown in FIGS. 1 and 2.

In both embodiments the functional operation is controlled by a central processing unit 26.

Incorporation of the CPR mode response into an ordinary analog digital watch format provides instantaneous access to accurate chest compression references to any person wearing the watch which will introduce these benefits throughout the community at large. It is thus a useful aid to CPR application both in the training classroom and in field use. As back-up timing support in critical or adverse situations, it will remove or minimise most of the stress and trauma associated with CPR application and neutralise distractions which are manifest in all in-field environments. It will also provide comfort and reassurance to the operator who uses it. Broad use of the device within the community may not only improve response results but also the quality of those results.

It will of course be realised that the above has been given only by way of illustrative example of the invention and that all such modifications and variations thereto as would be apparent to persons skilled in the art are deemed to fall within the broad scope and ambit of the invention as is defined herein in the appended claims.

We claim:

1. A watch assembly operable to provide aid for cardio-pulmonary resuscitation, said watch assembly comprising time keeping and time display means so that said watch assembly is operable in a time keeping mode, cardio-pulmonary resuscitation aid means so that said watch assembly is operable in a cardio-pulmonary resuscitation mode, and mode selection means operable for selecting said time keeping mode or said cardio-pulmonary mode, wherein said cardio-pulmonary resuscitation aid means includes:
chest compression indication means which provides recurring chest compression signals;
switching means for selecting a desired one of a plurality of chest compression signal rates indicated by identification means associated with said switching means;
pulmonary inflation indication means which provides regular pulmonary inflation signals in accordance with the selected chest compression signal rate;
counting means for counting the total number of chest compression signals;
timing means for recording the elapsed time corresponding to the total chest compression signals counted, and,
counting and timing display means for providing a visual display of the output of said counting means and said timing means, said watch assembly having a size and shape which allows said watch assembly to be worn on a wrist of a user.

2. A watch assembly operable to provide aid for cardio-pulmonary resuscitation as defined in claim 1, wherein said chest compression indication means includes an audible alarm for producing chest compression signals at said desired chest compression rate.

3. A watch assembly operable to provide aid for cardio-pulmonary resuscitation as defined in claim 2, wherein said chest compression indication means includes chest compression display means which provides a visual display corresponding to the selected desired chest compression signal rate.

4. A watch assembly operable to provide aid for cardio-pulmonary resuscitation as defined in claim 1, wherein said switching means includes three switch assemblies, each said switch assembly being provided with identification means.

5. A watch assembly operable to provide aid for cardio-pulmonary resuscitation as defined in claim 4, wherein said identification means includes the numerals 60, 80 and 100 applied to respective ones of said switch assemblies.

6. A watch assembly operable to provide aid for cardio-pulmonary resuscitation as defined in claim 5, wherein said each said switch assembly includes visual indicator means which when activated indicate an actuated switch assembly.

7. A watch assembly operable to provide aid for cardio-pulmonary resuscitation as defined in claim 6, wherein said visual indicator means and said audible alarm are simultaneously actuated.

8. A watch assembly operable to provide aid for cardio-pulmonary resuscitation as defined in claim 1, wherein said counting and timing display means provides a plurality of numerical displays, each said numerical display indicating the output of said counting means for each selected desired chest compression rate.

9. A watch assembly operable to provide aid for cardio-pulmonary resuscitation as defined in claim 8, including an analog/digital display having a second hand which sweeps a watch face divided into quarters whereby the watch may be used for checking pulse rates.

10. A watch assembly operable to provide aid for cardio-pulmonary resuscitation as defined in claim 1, wherein said cardio-pulmonary resuscitation aid means utilises integrated circuitry.

11. A watch assembly operable to provide aid for cardio-pulmonary resuscitation as defined in claim 10, including a plurality of function buttons.

12. A watch assembly operable to provide aid for cardio-pulmonary resuscitation as defined in claim 1, including a count down assembly for use when checking the pulse of a patient which provides a visual and audile indication upon the elapsing of a predetermined or preselected time period.

13. A watch assembly operable to provide aid for cardio-pulmonary resuscitation as defined in claim 12, wherein said preselected time period is 15, 30 and 60 seconds.

14. A watch assembly operable to provide aid for cardio-pulmonary resuscitation as defined in claim 1, including muting means adapted to vary the production of visual and audile indications in respect of both compression and inflation rates.

15. A watch assembly operable to provide aid for cardio-pulmonary resuscitation as defined in claim 14, wherein said plurality of function buttons includes an option for generating indications of a need to check the pulse of a patient.

16. A watch assembly operable for providing aid for cardio-pulmonary resuscitation, said watch assembly comprising time keeping and time display means so that said watch assembly is operable in a time keeping mode, cardio-pulmonary resuscitation aid means so that said watch assembly is operable in a cardio-pulmonary resuscitation mode, and mode selection means operable for selecting said time keeping mode or said cardio-pulmonary resuscitation aid mode, wherein said cardio-pulmonary resuscitation aid means includes:
  chest compression indication means for providing recurring chest compression signals;
  switching means for selecting a desired one of a plurality of chest compression signal rates indicated by identification means associated with said switching means;
  visual indicator means operatively associated with said switching means so that a respective one of said visual indicator means is activated when a chest compression rate is selected, said chest compression indication means and a respective one of said visual indicator means being simultaneously and repetitively activated at the selected desired chest compression rate, and
  pulmonary inflation indication means for providing regular pulmonary inflation signals in accordance with the selected chest compression signal rate,
said watch assembly having a size and shape which allows said watch assembly to be worn on a wrist of a user.

17. A cardio-pulmonary resuscitation aid including:
  compression indication means which provides recurring chest compression signals, said indication means having an audible alarm for producing chest compression signals at a selected desired chest compression rate and chest compression display means which provides a visual display corresponding to the selected desired chest compression signal rate;
  switching means for selecting a desired one of a plurality of chest compression signal rates indicated by identification means, said switching means having three switch assemblies each provided with identification means in the form of the numerals 60, 80 and 100 applied to respective ones of said switch assemblies and including visual indicator means simultaneously actuated with said audible alarm and which when activated indicate an actuated switch assembly;
  pulmonary inflation indication means which provides regular pulmonary inflation signals in accordance with the selected chest compression signal rate;
  counting means for counting the total number of chest compression signals;
  timing means which records the elapsed time corresponding to the total chest compression signals counted, and
  counting and timing display means which provides a plurality of numerical displays indicating the output of said counting means for each selected desired chest compression rate and the output of the timing means indicating the elapsed time corresponding to the total chest compression signals counted.

* * * * *